United States Patent [19]
Chamberlin et al.

[11] Patent Number: 5,942,537
[45] Date of Patent: Aug. 24, 1999

[54] METHOD OF INHIBITING THE TRANSPORT OF L-GLUTAMATE TO TREAT CNS DISORDERS

[75] Inventors: A. Richard Chamberlin, Irvine; Richard J. Bridges, Mesa; Carl W. Cotman, Santa Ana; Mark S. Stanley, Pacifica, all of Calif.

[73] Assignee: The Regents of the University of California, Oakland, Calif.

[21] Appl. No.: 08/104,417

[22] Filed: Aug. 9, 1993

Related U.S. Application Data

[63] Continuation of application No. 07/427,235, Oct. 25, 1989, abandoned.

[51] Int. Cl.$^6$ .......................... A61K 31/575; A61K 31/40
[52] U.S. Cl. .......................... 514/423; 514/91; 514/424; 514/425
[58] Field of Search .......................... 514/89, 422, 423, 514/424, 91, 425

[56] References Cited

U.S. PATENT DOCUMENTS

| Re. 28,141 | 8/1974 | Lumsford et al. | 514/408 |
|---|---|---|---|
| 3,458,635 | 7/1969 | Lumsford et al. | 514/408 |
| 4,559,358 | 12/1985 | Butler | 514/424 |
| 4,719,219 | 1/1988 | Arvedsson et al. | 514/317 |
| 4,761,405 | 8/1988 | Rzeszotarski et al. | 514/114 |
| 4,833,156 | 5/1989 | Sakakibara et al. | 514/424 |

OTHER PUBLICATIONS

Bridges et al., Brain Research 415:163–168 (1987).
Bridges et al., J. Neurochem. 48:1709–1715 (1987).
Ferkany and Coyle, J. Neurosci. Res. 16:491–503 (1986).
Davies et al., Neuropharmacology 24:177–180 (1985).
King and Wheal, Eur. J. Pharmacol. 102:129–134 (1984).
Jais et al., Comp. Biochem. Physiol. 77C:385–389 (1984).
Capasso et al., Can. J. Chem. 61:2657–2664 (1983).
Roberts and Watkins, Brain Research, 85:120–125 (1975).
Bridges et al., Brain Research 415:163–168 (1987).
Bridges et al., J. Neurochem. 48:1709–1715 (1987).
Ferkany and Coyle, J. Neurosci. Res. 16:491–503 (1986).
Davies et al., Neuropharmacology 24:177–180 (1985).
King and Wheal, Eur. J. Pharmacol. 102:129–134 (1984).
Jais et al., Comp. Biochem, Physiol. 77C:385–389 (1984).

*Primary Examiner*—Theodore J. Criares
*Attorney, Agent, or Firm*—Campbell & Flores LLP

[57] ABSTRACT

A method of inhibiting the transport of a neurotransmitter away from the synapse comprising contacting a neurotransmitter transporter with a compound having the structure

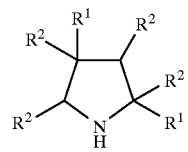

wherein

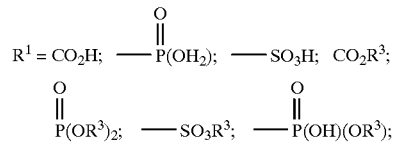

or $CONHR^3$ in any combination and and wherein $R^2=OR^3$, $NR^3_2$, alkyl, or substituted alkyl and $R^3$=alkyl or substituted alkyl.

7 Claims, 4 Drawing Sheets pyrrolidine-2,4-dicarboxylate

L-glutamate, 15

L-*trans*-PDC, 16 dihydrokainate, 17

METHOD OF INHIBITING THE TRANSPORT OF L-GLUTAMATE TO TREAT CNS DISORDERS

This application is a continuation of application Ser. No. 07/427,235, filed Oct. 25, 1989, now abandoned.

This invention was made with Government support under Grant Nos. NS-25401 and NS-01227 awarded by the National Institutes of Health and under Contract No. DAAL-03-86-K0067 awarded by the U.S. Army. The Government has certain rights in this invention.

BACKGROUND OF THE INVENTION

L-Glutamate is one of the most abundant excitatory neurotransmitters in the mammalian brain and, as such, is responsible for the majority of synaptic transmission in the central nervous system. Despite the fact that this acidic amino acid is known to interact with binding sites on a number of different proteins (excitatory neurotransmitter receptors, transport systems, and enzymes) during the process of neurotransmission, specific structural details of these interactions are lacking.

Considerable evidence has firmly established the existence of several classes of postsynaptic receptors through which the excitatory action of L-glutamate is mediated, as well as the presence of a high affinity transport system that terminates the resultant excitatory signal. In vivo, endogenous L-glutamate or a glutamate-like molecule binds to each of these sites, while in vitro, various glutamate analogues exhibit selective affinities and thus can pharmacologically differentiate among individual receptor classes. Specifically, three major types of excitatory amino acid transmitter receptors have been distinguished by their characteristic interactions with various agonists: N-methyl-D-aspartate (NMDA), kainate (KA), and quisqualate (QA). Despite the fact that these analogues have been invaluable in identifying and characterizing the various classes of transmitter receptors empirically, a unified model to explain the observed binding specificities in terms of specific molecular conformations has been elusive.

Unlike systems that depend upon rapid chemical degradation for transmitter signal termination, L-glutamate is removed from the synaptic cleft by high affinity transport. Again, little is known about the conformational requirements of substrate binding to this transport system, although several competitive inhibitors have been identified. Interest in the functional characteristics of this uptake mechanism has dramatically increased with the recent finding that excessive levels of glutamate (as well as other excitatory agonists) are neurotoxic and appear to play a significant role in neurological disorders such as ischemia, hypoglycemia, epilepsy, Huntington's disease and Alzheimer's disease.

Thus, the discovery of additional compounds which affect the transport system are critical to understanding the transport system and would be useful as therapeutics for treatment of the various disorders associated with the transport system. Applicants have satisfied this need with the discovery of compounds which are potent and selective inhibitors of the high affinity transport of L-glutamate.

SUMMARY OF THE INVENTION

A method of inhibiting the transport of a neurotransmitter away from the synapse comprising contacting a neurotransmitter transporter with a compound having the structure

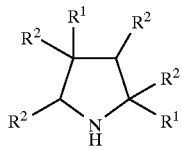

wherein

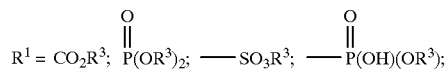

or $CONHR^3$ in any combination and $R^2=OR^3$, $NR^3{}_2$, alkyl, or H; and and $R^3$=alkyl substituted alkyl or H.

DETAILED DESCRIPTION OF THE INVENTION

Figure 1:
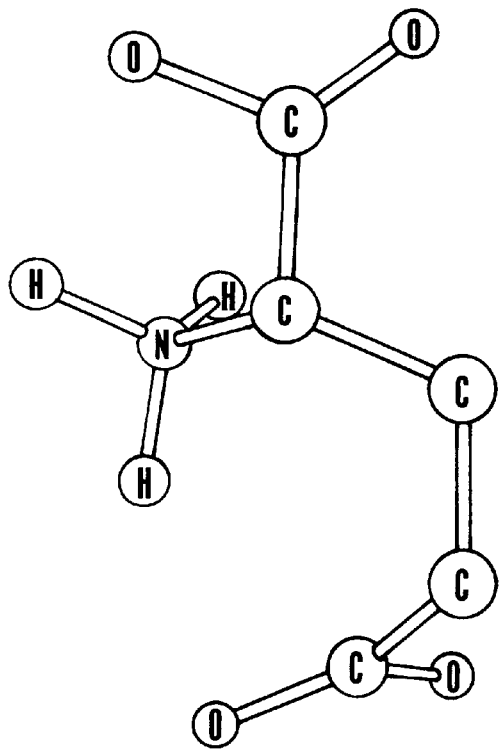
FIG. 1 shows a comparison of L-glutamate, L-trans-2,4-PDC, and Dihydrokainate.
Figure 1:
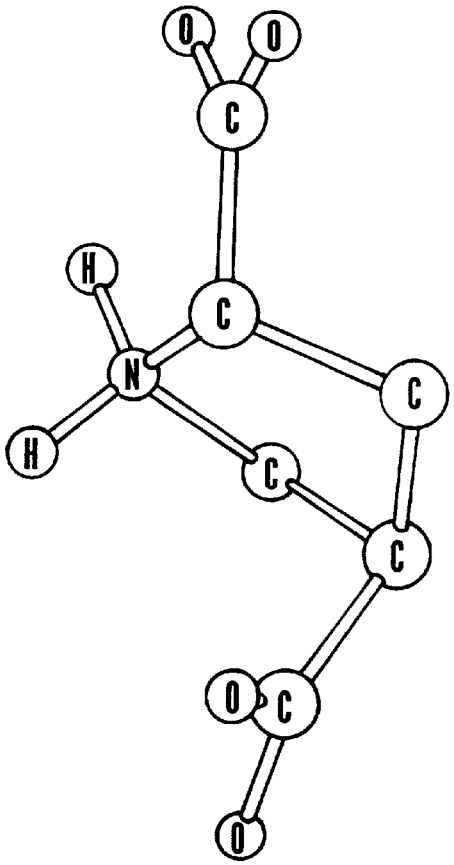
Figure 1:
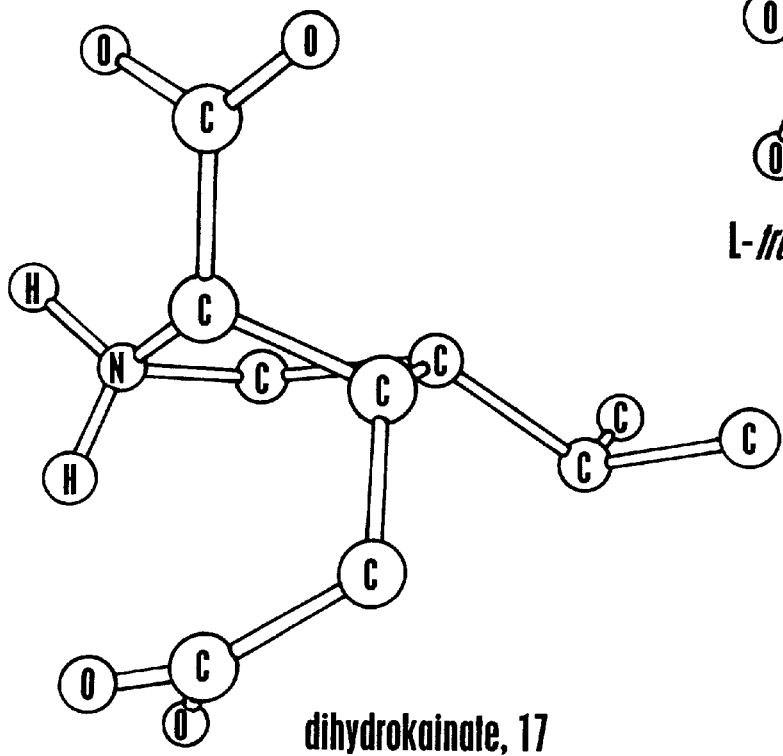

As an endogenous neurotransmitter, L-glutamate interacts with several different proteins during the course of synaptic transmission. These interactions include the multiple receptors mediating synaptic responses as well as the transport system that is responsible for clearing L-glutamate from the synaptic cleft and terminating its excitatory signal. Presumably these proteins each bind a specific L-glutamate conformer(s), since conformationally biased analogues interact with the individual sites with differing selectivities, thereby discriminating among binding sites on the various proteins (receptors, transport proteins, enzymes, etc.). This hypothesis is further supported by the present results, which show that L-trans-pyrrolidine-2,4-dicarboxylate (hereinafter "L-trans-2,4-PDC") is a potent inhibitor of sodium-dependent glutamate transport but does not appreciably bind to the three classes of excitatory glutamate receptors. Based on this selectivity, L-trans-2,4-PDC embodies specific structural/conformational characteristics necessary for binding to this uptake system that are distinct from those required for binding to the N-methyl-D-aspartic acid (NMDA), kainic acid (KA), and quisqualic acid (QA) receptors.

While the exact nature of transporters of L-glutamate are not known, the transporters are universally believed to be proteins. Thus, the transporters will be referred herein to as proteins. However, it is understood that the invention encompasses inhibiting the transporter regardless of its actual composition so long as the compounds of the invention bind the transporter.

The inhibition of glutamate transport in normal CNS tissue can have profound physiological consequences. While previous studies have demonstrated that the excitatory action of added L-glutamate is prolonged by co-administration of transport inhibitors, a major reduction in transport capacity would result in the accumulation of potentially excitotoxic levels of L-glutamate in the synaptic cleft. On the other hand, the inhibition of glutamate transport also can augment a compromised pathway by increasing the half-life of the transmitter in the synaptic cleft.

The availability of specific inhibitors of L-glutamate uptake provides useful probes for evaluating the role of the transport system in neurotransmission. This invention demonstrates that the strategy of utilizing conformationally well-defined, relatively rigid PDCs as glutamate conformer mimics is one that provides a new understanding of the chemical basis of selective binding to not only the uptake system, but to the excitatory receptors as well.

Thus, the present invention provides a method of inhibiting the transport of a neurotransmitter away from the synapse comprising contacting the neurotransmitter with a compound having the structure

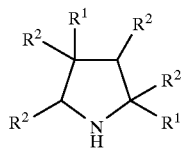

wherein $R^1=$

or $CONHR^3$ in any combination and and wherein $R^2=OR^3$, $NR^3{}_2$, alkyl, or H, and and $R^3$=alkyl substituted alkyl or H.

The invention is specifically demonstrated by the inhibition of L-glutamate away from the synapse. However, one skilled in the art would recognize that the compounds which bind L-glutamate would also bind L-glutamate like compounds, such as L-aspartate, cysteic acid, homocysteic acid and other excitatory amino acid analogs which can also act as neurotransmitters. Thus, the only criteria is that the inhibited compound is a neurotransmitter which binds to the same transport system as the compounds of the invention.

The invention shows the efficacy of such compounds by specifically demonstrating the efficacy of L-transpyrrolidine-2,4-dicarboxylate. The alternative compounds would also have a similar efficacy as they maintain the essential conformation necessary for such efficacy.

The invention also provides a method for treating a condition or pathology associated with an L-glutamate, or L-glutamate like molecule, deficiency comprising administering one or more of the above-recited compounds. These deficiencies can contribute to motor dysfunction, memory loss, or other central nervous system defects in aging, trauma, and degenerative diseases such as Alzheimer's or Huntington's Disease.

The invention provides a method for enhancing the excitatory signal of L-glutamate in damaged pathways by increasing its half-life in the synaptic cleft. In conditions such as stroke, degenerative diseases, trauma to either brain tissue or spinal cord there is a loss of excitatory pathway function. By inhibiting the removal of L-glutamate, the excitatory signal of the transmitter is enhanced and can compensate for the decreased release and weakened signal.

The invention also provides a method for reducing or blocking the release of potentially neurotoxic L-glutamate from cells that have been energetically compromised by pathological conditions and preventing the associated secondary pathology. Current models of uptake processes indicate that the transporter proteins act much like "turnstiles" in assisting the movement of substrate molecules across the membrane and into the cell. In this respect, substrates can move in either direction across the cell membrane. To concentrate a compound, such as L-glutamate, inside the cell a significant amount of energy must be spent (i.e., active transport). If the energy levels are drained, as is thought to accompany pathological conditions (anoxia, ischemia, trauma, seizures) then the intracellular glutamate would be released from the cell by the reverse action of the transport protein. If, however, L-trans-2,4-PDC or a similar derivative is identified as an inhibitor of the transport system but not a true substrate for uptake, this compound would bind to the transport protein and lock its binding site in an extracellular direction. In effect, this would jam the transport system and slow or prevent the release of glutamate from the cell by physically blocking the membrane transport. The ability to decrease this release would attenuate the pathological damage associated with extracellular glutamate excitotoxicity.

The invention further provides a mechanism to identify the chemical properties required to interact with the transporter protein. Owing to the enantiomeric purity and restricted conformations of the L-glutamate analogues prepared (all D,L,cis and trans isomers), the three dimensional characteristics of the functional groups on these analogues can be defined. Thus, not only has a potent inhibitor of glutamate transport been synthesized and identified, but the chemical requirements necessary to bind to the transporter have also been defined. In this way, the conformation data generated as a result of the binding studies with L-trans-2,4-PDC serve as an important model in the design of other derivatives aimed at binding to the transporter. This modeling of the binding site was not previously possible because previous compounds were not pure or were conformationally too flexible. Thus, any moiety which has the conformation for binding to a glutamate transporter of L-trans-2,4-PDC or its analogs can be made and used for the same function. Thus, not only L-glutamate, but other known transport inhibitors should be capable of assuming similar geometries. To test this concept, MMX-minimized conformations of L-glutamate, L-trans-PDC, and dihydro-kainate (a previously identified transport inhibitor) were compared by calculating the mean deviation of atoms (Cl, Cα, N, and distal carboxyl) for pairs of conformational minima. As shown in FIG. 1, there is considerable homology among specific conformations of each of these acidic amino acids (each conformer is aligned such that the carboxyl-C2 bond lies along the y-axis. The L-glutamate conformer 15 is a local minimum structure that closely resembles an all-staggered conformation reported to be present in approximately 20% abundance in solution. The corresponding L-trans-PDC 16 is one of several possible envelope conformers, in this case with the distal carboxyl group situated near the a-amino substituent. Although one instinctively tends to superimpose the pyrrolidine rings when visually comparing conformers of L-trans-PDC and dihydrokainate, a satisfactory match among the functional groups is achieved only when the proline rings themselves are not aligned, as in 16 vs 17. All three of these conformations (15, 16, and 17) are characterized by placement of the two carboxyl groups in a folded array such that the distance separating the carboxyl carbons is 4.5±0.1A. and the distal carboxyl-to-N distance is 2.9±0.1A. Since this arrangement of functionality is not suitable for efficient binding to any of the excitatory receptors, selective interaction with the transport protein can now be accounted for at the molecular level in terms of these geometries.

The invention also provides a mechanism to selectively kill organisms which are susceptible to excitatory amino acid receptor agonists. Excitatory amino acid receptor agonists have long been known to be toxic to certain invertebrates. The best example of which is kainic acid, which was originally described as an anti-ascaris (intestinal worm) drug. T. Takamoto, In: Kainic Acid as Tool in Neurobiology, Ed. McGeer et al., Raven Press, N.Y. (1978) incorporated by reference herein. The ability of L-trans-2,4-PDC to inhibit the removal of L-glutamate would also be toxic as it would produce an excessive accumulation of extracellular excitatory agonists. Therefore, these transport inhibitors would be useful as a toxin to invertebrates.

The method can be effective since, as taught herein, the provided compounds can inhibit the transport of L-glutamate from the synapse. Since the subject compounds competitively inhibit the removal of L-glutamate, the L-glutamate remains in the synapse and can bind receptors in neurological transmissions and thus overcome the effects of L-glutamate deficiency. The means of administering the compounds of the invention are known to those skilled in the art and can readily be altered for increased efficacy. Examples include aqueous suspensions, containing conventional suspending agents, dispersing agents, or wetting agents' preservatives, color agents, flavoring agents, or sweetening agents may be formulated in accordance with industry standards. Similarly, dispersible powders and granules for preparation of aqueous suspensions by the addition of water may be provided.

The optimal concentration of the above-recited compounds is a function of a variety of factors, such as desired frequency of application, mode of application (orally, intraperitoneally, intravenous, or direct application to CNS tissue during surgery) duration of effect, amount of repair and/or protection required, severity of disease or trauma, result of toxicology studies, or the level of adverse side effects and considerations implicated by the chemical nature of the compounds or their carriers.

The effective dose of the above-recited compounds, as anticipated in this invention, is between 0.01 mg/kg to 100 mg/kg; preferably, between 0.5 mg/kg and 10 mg/kg; and most preferably, between 0.5 mg/kg and 5 mg/kg. The effective dosage of the compounds for any particular application may be readily determined by standard animal and clinical testing techniques. However, the dosage unit composition will contain pharmaceutically-effective amounts of the active ingredient.

The following examples merely illustrate the invention and thus are not intended to be limiting. Additionally, the examples include numerical reference to specific structures recited in the figures.

EXAMPLE I

Chemistry

Figures 1, 2:
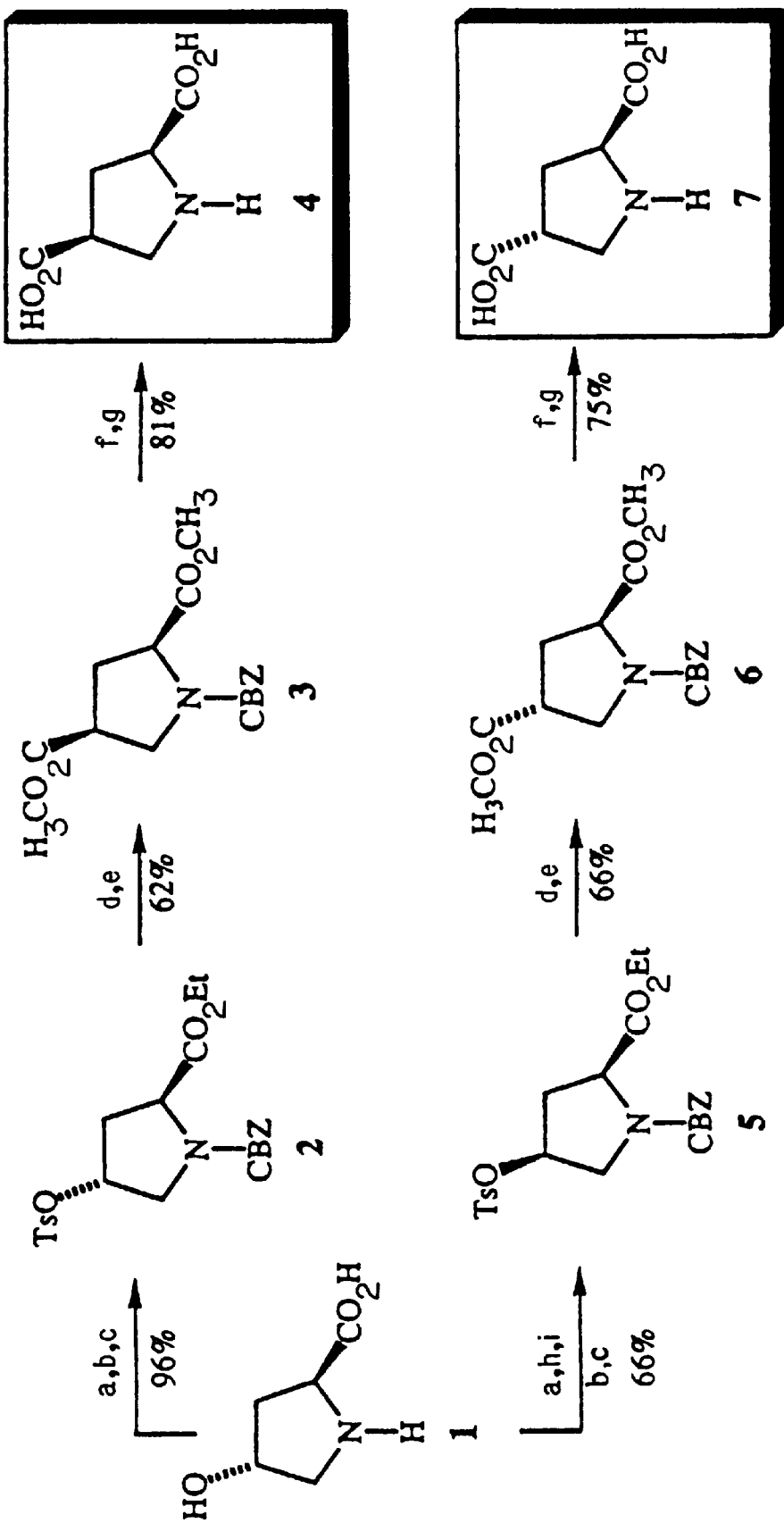
FIG. 2 shows the synthesis of PDC Diastereomers.
Figure 2:
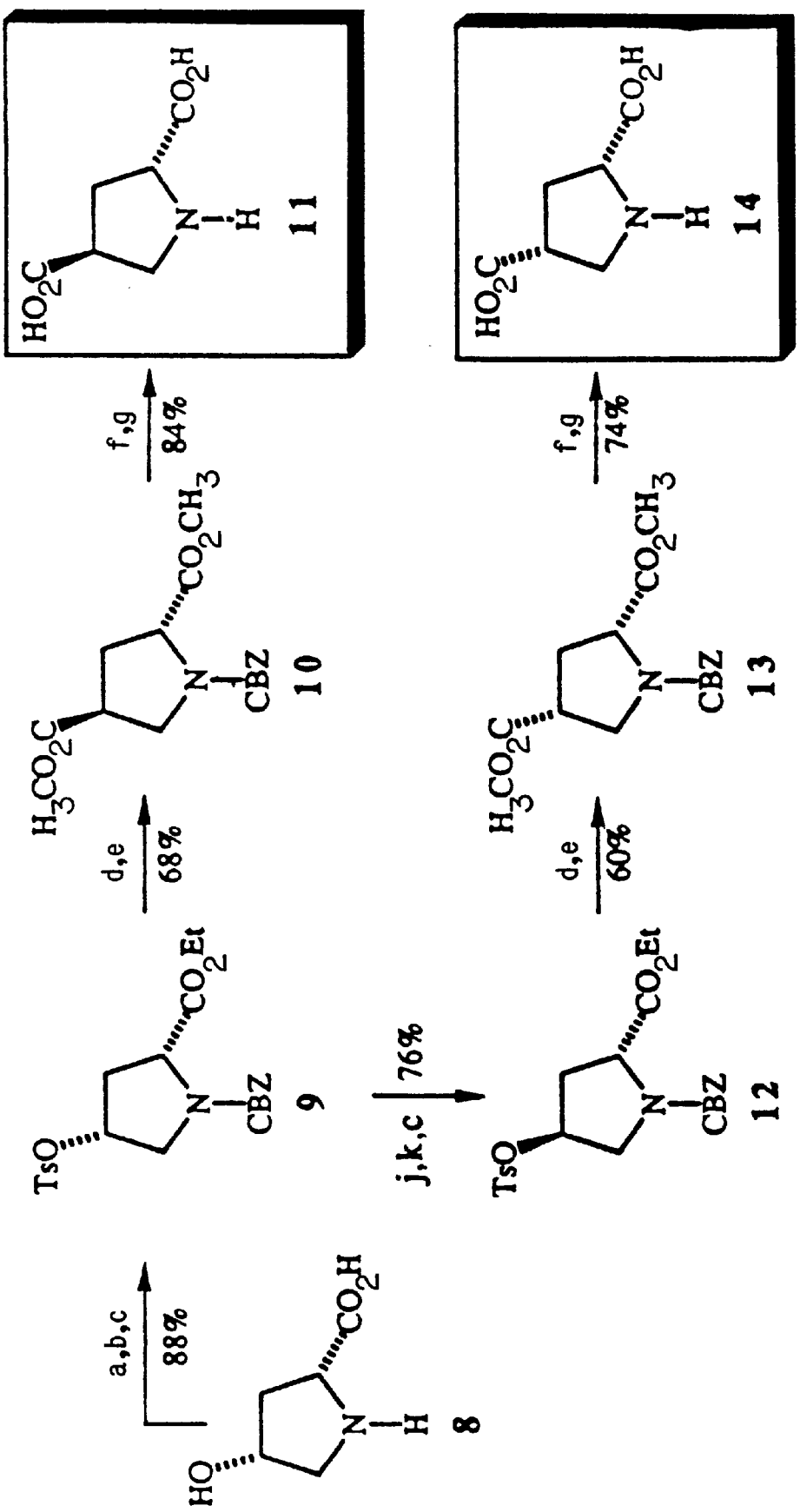

The cis and trans L-pyrrolidine 2,4-dicarboxylates, 4 and 7 respectively, were synthesized from commercially available trans-4-hydroxy-L-proline (FIG. 2). For the synthesis of 4, the starting proline derivative 1 was converted into the protected tosylate 2 by sequential reaction with CBZ chloride, ethanolic tosic acid, and tosyl chloride/pyridine. $S_N2$ displacement of the tosyl group with cyanide gave the cis nitrile ethyl ester, which underwent a Pinner reaction and transesterification in wet methanol to give 3, followed by saponification of the resultant diester and finally hydrogenolysis to give 4 in an overall yield of 47%. The cis tosylate ethyl ester 5 required for the preparation of the trans diacid 7 was readily prepared by Jones oxidation of N-CBZ-trans-4-hydroxy-L-proline and stereoselective reduction of the resultant ketone with $NaBH_4$. Esterification and tosylation then gave 5 in 66% yield. Conversion of this tosylate into 7 was brought about in 49% yield by the aforementioned four step displacement/Pinner/deprotection sequence.

Cis-4-hydroxy-D-proline 8 serves as starting material for both D-diacids 11 and 14. Following the procedure for the conversion of 1 into 4, the cis tosylate ethyl ester 9 was prepared in three steps (88%) from 8, and the four step conversion of a tosylate ethyl ester (in this case 9) into the corresponding 2,4-pyrrolidine dicarboxylate afforded trans-4-carboxy-D-proline 11 (56%). The alcohol inversion sequence in this case differs from that described above because the available D-starting material is the cis diastereomer rather than trans. Hence, the C-4 tosylate group in the ester 9 was inverted by $S_N2$ displacement of the tosyl group with n-$Bu_4NOAc$, hydrolysis of the resultant acetate with NaOEt in ethanol, and tosylation of the inverted alcohol group, giving the trans ester 12 in 76% yield. Subjecting 12 to the aforementioned four step process gave 14 in 44% yield from 12. The enantiomeric purities of the target diacids, determined by comparison of the $^1H$ NMR spectra of the Mosher amides prepared from the N-deprotected dimethyl esters 3, 6, 10 and 13, were >95% in each case Dale, J. A. et al., J. Org. Chem. 34:2543 (1969) incorporated by reference herein. The final diacid products showed no sign of epimerization during deprotection, indicating that both stereochemical labile centers survive intact.

EXAMPLE II

Pharmacology

Figure 3:
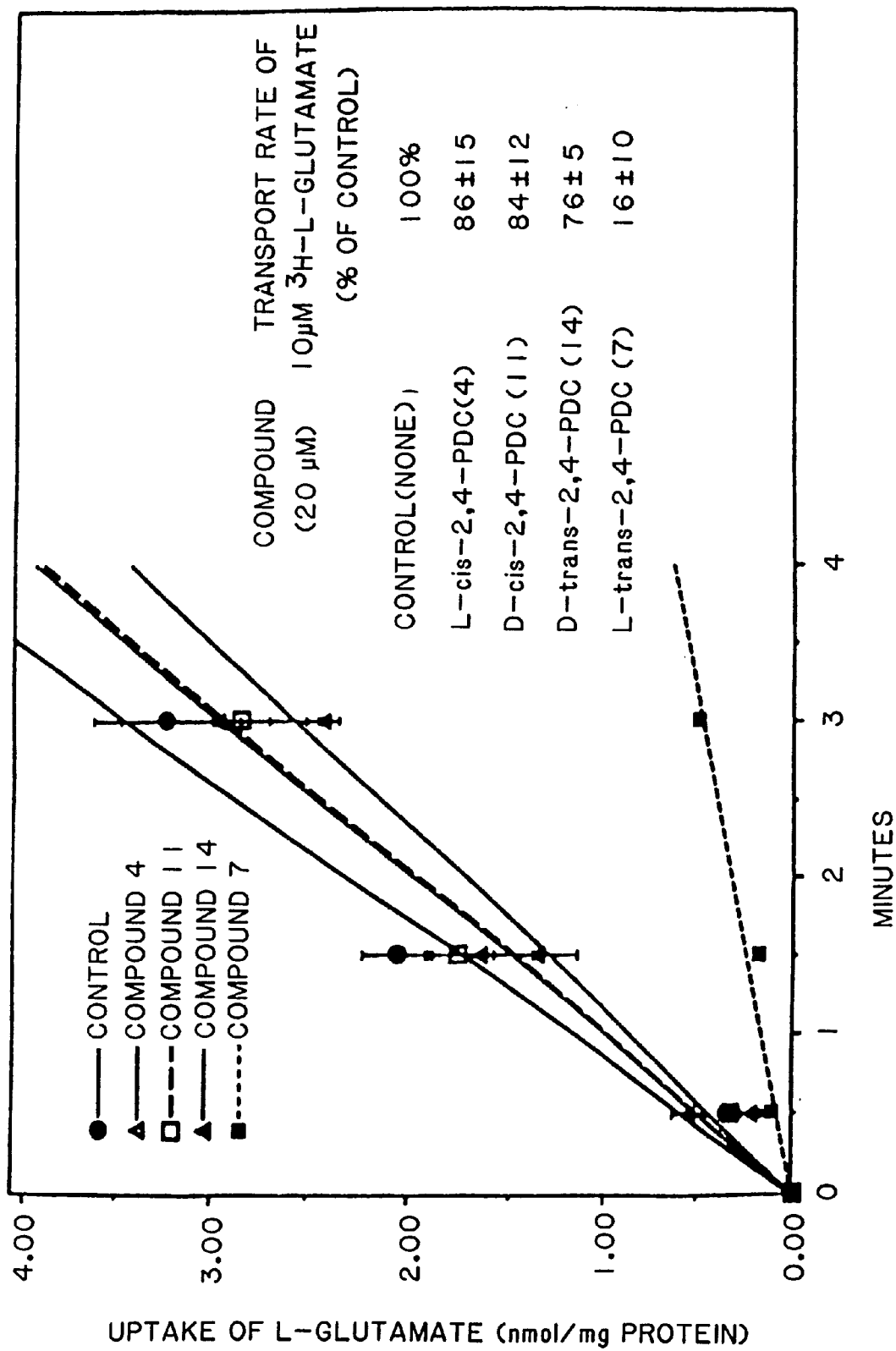
FIG. 3 shows the inhibition of L-glutamate transport into synaptosomes by L-trans-2,4-PDC. Synaptosomal uptake of $^3$H-L-glutamate (10 $\mu$M) was followed at 37° C. in the presence and absence of 20 $\mu$M PDC isomers. The curves shown are from representative experiments (n=2–4 rate determinations) and are reported as mean ±SD. Transport rates were determined by linear regression analysis and have been corrected for background and non-specific uptake. The effect of the PDC isomers and is reported as % of control transport rate ±SD (n=8–16 rate determinations).

The Synaptosomes were prepared by the procedure of (a) Booth, R. F. G.; Clark, J. B., Biochem J. 176, 365 (1978) and assayed for synaptosomal uptake as described by (b) Kuhar, M. M.; Zarbin, M. J., Neurochem 31, 251 (1978), both which are incorporated by reference herein. The binding specificities of the four PDC isomers were determined by testing both their ability to inhibit the high affinity transport of $^3H$-L-glutamate into synaptosomes and to block the binding of radioligands to each of the three receptor sites in a synaptic plasma membrane preparation (SPM) (Synaptic plasma membranes were prepared and NMDA receptor binding quantified as described by Monaghan, D. T.; Cotman, C. W., Proc. Nat. Acad. Sci. U.S.A. 83, 7532 (1986) incorporated by reference herein). When included in the $^3H$-L-glutamate uptake assay, as represented in FIG. 3, at only a 2-fold excess relative to L-glutamate (10 $\mu M$ of $^3H$-L-glutamate vs. 20 $\mu M$ of 7), the L-trans-2,4-PDC isomer reduced the rate of synaptosomal transport from control levels of 1.13 nmol $min^{-1}$ mg-$protein^{-1}$ to 0.16 nmol $min^{-1}$ mg-$protein^{-1}$. These values represent more than an 80% reduction in the rate of uptake, indicating that the compound interacts with the transport protein with an affinity at least as great as that of L-glutamate itself. In contrast, when the L-cis, D-cis, and D-trans isomers were included at similar concentrations they were found to be substantially less effective. This selective inhibition by L-trans-2,4-PDC clearly delineates a preferred configurational and/or conformational relationship for binding to the glutamate uptake protein.

To further characterize the pharmacological specificity of the PDC conformers and identify other potential sites at which the transport inhibitor could bind, the compounds were tested for their ability to inhibit the binding of $^3$H-L-glutamate to NMDA receptors, $^3$H-KA binding to KA receptors, and $^3$H-AMPA (α-amino-3-hydroxy-5-methylisoxazole-4-propionic acid) binding to QA receptors. Binding to kainate receptors was quantified by the procedures of (a) Simon, J. R.; Contrera, J. F.; Kuhar, M. J., J. Neurochem 26, 141 (1976), and (b) London, E. D.; Coyle, J. T.; Molec. Pharm. 15, 492 (1979) which are incorporated by reference herein. Binding to quisqualate receptors (QA) were quantified as described by (c) Honore, T.; Lauridsen, J.; Krogsgaard-Larsen, P. J., Neurochem 1982, 38, 173, which are incorporated by reference herein. As is reported in Table 1, only D-trans-PDC proved to exhibit any inhibitory activity, weakly inhibiting the binding of $^3$H-L-glutamate to the NMDA receptor. Notably, L-trans-2,4-PDC did not significantly inhibit radioligand binding to any of the three receptors even when present in $10^4$-fold excess. This lack of interaction with any of the excitatory receptors is in direct contrast with its potent inhibition of transport and identifies L-trans-2,4-PDC as a specific probe of the L-glutamate transport system.

TABLE 1

Competitive Binding Studies for Diacids 4, 7, 11, and 14

| DIACID (Conc.) | $^3$H-AMPA binding to QA receptors | $^3$H-KA to binding KA receptors % of Control | $^3$H-L-GLU binding to NMDA receptors |
|---|---|---|---|
| Control | 100 | 100 | 100 |
| 4 (100 μM) | 102 ± 12 | 100 ± 12 | 89 ± 13 |
| 7 (100 μM) | 109 ± 13 | 102 ± 10 | 87 ± 10 |
| 11 (100 μM) | 108 ± 11 | 92 ± 6 | 95 ± 12 |
| 14 (100 μM) | 110 ± 9 | 101 ± 6 | 38 ± 12 |
| (20 μM) | — | — | 76 ± 5 |

The binding data in the Table is reported as % of control binding ± the s.d. The binding assays were performed as described above and have been corrected for non-specific binding.

EXAMPLE III

Synaptosomal Uptake of Glutamate

Synaptosomes were prepared by the procedure of Booth et al., (Biochem J. 176:365 (1978) incorporated by reference herein), using Ficoll/sucrose gradient centrifugation. Uptake of $^3$H-L-glutamate was followed essentially as described by Kuhar and Zarbin (J. Neurochem 31:25 (1978) incorporated by reference herein.) Synaptosomes were suspended in a physiological buffer (Krebs-Ringer phosphate buffer) and preincubated at 37° C. for 5 min. The uptake assay was initiated by the addition of $^3$H-L-glutamate (0.1–100 μM). Aliquots were removed at appropriate times (0.5–10 min) and were rapidly filtered on GF/F glass fiber filters. The filters were rapidly washed with 20 volumes of ice cold buffer. Radioactivity present on the filters was determined by liquid scintillation counting. Uptake rates were corrected for both background (i.e., uptake at 0 min) and leakage (i.e., uptake at 0° C.).

EXAMPLE IV

Excitatory Amino Acid Receptor Binding

Synaptic plasma membrane (SPMS) were prepared as previously described (Monaghan, D. T.; Cotman, C. W., Proc. Nat. Acad. Sci. U.S.A. 83:7532 (1986) incorporated by reference herein.) Briefly, male Sprague-Dawley rats (200 g) were decapitated, their forebrains were rapidly removed, and the brain tissue homogenized in 0.32M sucrose. Following differential centrifugation, a membrane fraction enriched in synapses, but low in myelin and mitochondria, was obtained. This membrane fraction was washed three times with 200 μM Tris-acetate buffer, pH 7.2, and diluted into the appropriate assay buffer to about 200 μg protein/ml.

Binding to NMDA, KA, and QA receptors were quantified with $^3$H-L-glutamate, $^3$H-KA, and $^3$H-AMPA respectively. The binding assays were carried out using optimally selective conditions of time, temperature, and buffer for each of the three receptor classes. $^3$H-L-Glutamate binding was quantified under conditions that selectively label NMDA receptors. The SPMs were incubated with $^3$H-L-glutamate (10 nM, 50.9 Ci/mmol) in 50 mM Tris-acetate, pH 7.0, at 4° C. for 30 minutes. Non-specific binding was determined by the inclusion of 500 μM L-glutamate. KA receptors were quantified as previously described. $^3$H-KA (10 nM, 60 Ci/mmol) binding was determined in 50 mM Tris-citrate buffer, pH 7.0, at 4° C. for 30 min. Non-specific binding was determined by the inclusion of 100 μM unlabeled KA. QA receptors were measured with $^3$H-AMPA binding as described by Honore et al. J. Neurochem. 38:173–178 (1982). Essentially, 3 H-AMPA (10 nM, 27.6 Ci/mmol) binding is quantified in 50 mM Tris-acetate buffer, pH 7.2, containing 100 mM KSCN for 30 minutes at 4° C. Non-specific binding was determined by the inclusion of 100 μM quisqualic acid. In the inhibition studies, the conformationally defined analogues were included in the assay mixture at the appropriate concentrations (0.1–200 μM). The assays (total volume, 1.08 mL) were initiated by the addition of radiolabel and terminated by centrifugation (Beckman Microfuge, top speed, 3 min). Unbound radioligand in the supernatant was removed by suction and the radioactivity in the pellet quantified by liquid scintillation counting. All of the binding studies were carried out as 2 sets of triplicates within a single experiment and each experiment was repeated at least 3 times.

EXAMPLE V

Chemical Synthesis

GENERAL METHODS. Proton and carbon-13 magnetic resonance (NMR) spectra were measured, as specified, on either a Bruker WM 250 (250 MHz) or a General Electric QE-300 (300 MHz) spectrometer. For spectra measured in organic solvents, data are reported in ppm from internal tetramethylsilane for $^1$H NMR and in ppm from the solvent in $^{13}$C NMR. For spectra taken in $D_2O$, data are reported in ppm from internal 3-(trimethylsilyl)propionic acid, sodium salt for both $^1$H NMR and $^{13}$C NMR. Data are reported as follows: chemical shift, multiplicity (app=apparent, s=singlet, d=doublet, t=triplet, q=quartet, m=multiplet, br=broad), coupling constant, and integration. Infrared (IR) spectra were taken with a Perkin-Elmer Model 283 spectrophotometer. Mass spectra (MS) were measured on a Finnegan 9610 spectrometer. High resolution mass spectra (HRMS) were determined on a VG analytical 7070E spectrometer. Optical rotations were obtained on a Perkin-Elmer 241 MC polarimeter of a JASCO DIP-360 digital polarimeter. Melting points (mp) were taken on a Laboratory Devices Mel-Temp melting-point apparatus and are reported uncorrected. Elemental analyses were performed by Galbraith Laboratories, Knoxville, Tenn.

Dry tetrahydrofuran (THF) and ethyl ether ($Et_2O$) were distilled from calcium hydride and deperox molecular sieves (Fluka, Ronkonkoma, N.Y.). All inert atmosphere operations were done under argon passed through a Drierite drying tube in oven or flame dried glassware. Unless otherwise noted, all organic layers from extractive workups were dried over $MgSO_4$ or $Na_2SO_4$, filtered, and the solvent removed on a rotary evaporator. Thin-layer chromatography (TLC) was performed on 0.25 mm Merck precoated silica gel plates (60 F-254). Flash chromatography was performed on ICN 200–400 mesh silica gel.

N-Benzyloxycarbonyl)-trans-4-hydroxy-L-proline. Trans-4-hydroxy-L-proline 1 (10.0 g, 76.3 mmol) and $NaHCO_3$ (16.0 g, 190 mmol) were dissolved in $H_2O$ (165 mL), then a solution of benzyl chloroformate (12.5 mL, 15.0 g, 87.7 mmol) in toluene (40 mL) was added over a period of 15 minutes. After stirring at room temperature for 16 h, $CO_2$ evolution had ceased and the two phases were separated. Excess benzyl chloroformate was removed from the aqueous phase by washing with ether (4×50 mL). Cooling of the aqueous phase in an ice bath, followed by acidification to pH 2 with concentrated HCl, caused the oily product to precipitate. This oil was extracted into ethyl acetate by repeated washings (5×50 mL) of the aqueous layer. Further acidification of the aqueous layer produced no more precipitate, indicating thorough removal of the product. The combined organic extracts were dried ($MgSO_4$) and concentrated to a viscous oil, which crystallized upon standing at room temperature to provide 19.9 g (98%) of N-CBZ-trans-4-hydroxy-L-proline: mp 106°–107° C. (lit.[19]mp 106°–107° C.); $[\alpha]^{24}D^{-77.5°}$ (c 1.03, $CHCl_3$) [lit.[19] $[\alpha]^{20}$ $D^{-72°}$ (c 1.0 $CHCl_3$)].

N-(Benzyloxycarbonyl-trans-4-hydroxy-L-proline ethyl ester. N-CBZ-trans-4-hydroxy-L-proline (5.00 g. 18.8 mmol) and p-toluenesulfonic acid monohydrate (0.36 g, 1.9 mmol) were dissolved in ethanol (300 mL) and the reaction mixture heated at reflux with the collection of wet ethanol in a Dean-Stark trap. After 16 h, the trap was emptied whenever full until the total reaction volume had decreased to about 50 mL, then the tosic acid was neutralized with an excess of $NaHCO_3$ (0.8 g. 10 mmol). Volatiles were removed in vacuo, the residue was diluted with ethyl acetate (100 mL) and the mixture stirred for 0.5 h or until the salts were free of oil. Solids were removed by filtration through Celite-$K_2CO_3$ and the filter cake was washed with ethyl acetate (50 mL). Concentration of the combined filtrate and washings in vacuo provided 5.6 g (100%) of the crude trans hydroxy ester as a thick pale yellow oil of sufficient purity to be used in the next step without further purification: TLC $R_f$ 0.07 (5:3 $Et_2O$-petroleum ether); $[\alpha]^{25}_D-60°$ (c 1.04, $CHCl_3$); $^1H$ NMR (250 mHz, $CDCl_3$) δ 7.35–7.27 (m, 5 H), 5.18–4.99 (m, 2 H, $PhCH_2$), 4.52–4.46 (m, 2 H, H-2 and H-4), 4.20–4.01 (q, J=7.1 Hz, 2 H, $CO_2CH_2CH_3$, two rotamers), 3.71–3.52 (m, 2 H, H-5), 2.8–2.74 (bs, 1 H, OH), 2.38–2.23 (m, 1 H, H-3), 2.12–2.00 (m 1 H, H-3), 1.26–1.10 (t, J=7.1 Hz, 3 H, $CO_2CH_2CH_3$, two rotamers); $^{13}C$ NMR (75.5 MHz, $CDCl_3$) δ 172.74, 172.55, 154.98, 154.60, 136.35, 136.11, 128.38, 128.31, 127.93, 127.77, 127.72, 69.94, 69.20, 67.22, 67.14, 61.27, 61.14, 57.99, 57.76, 55.16, 54.56, 39.09, 38.33, 14.04, 13.92; IR ($CHCl_3$) 3620–3200 (broad), 2990, 1737, 1700, 1420, 1355, 1190, 1170 $cm^{-1}$; LRMS (CI, 70 eV, isobutane) m/e 294 ($MH^+$, 100), 250 (83), 220 (19), 158 (18), 91 (58); HRMS (EI, 70 eV) m/e 293.1260 (293.1263 calcd for $C_{15}H_1NO_5$).

N-(Benzyloxycarbonyl)-trans-4-tosyloxy-L-proline ethyl ester (2). To a solution of N-CBZ-trans-4-hydroxy-L-proline ethyl ester (5.6 g, 19 mmol) and anhydrous pyridine (4.6 mL, 4.5 g, 57 mmol) in $CHCl_3$ (30 mL) was added p-toluenesulfonyl chloride (7.2 g, 38 mmol) in one portion. After stirring at room temperature for 72 h, the reaction was diluted with $CH_2Cl_2$ (70 mL) and pyridine removed by repeated extraction with 10% HCl (4×10 mL). The organic layer was dried ($MgSO_4$) and concentrated to a golden oil which was purified by silica gel flash chromatography (gradient elution, using 1:1, 2:1 ethyl ether-petroleum ether) to yield 8.2 g (98%) of pure 2 as a colorless oil: TLC $R_f$ 0.27 (3:3:1 ethyl ether-petroleum ether-$CH_2CL_2$); $[\alpha]^{24}_D-29°$ (c 1.5, $CHCl_3$); $^1H$ NMR (250 MHz, $CDCl_3$ δ 7.79–7.74 (m, 2 H), 7.37–7.26 (m, 7 H), 5.18–5.00 (m, 3H, $phCH_2$ and H-4), 4.44 (app q, J=7.5 Hz, 1 H, H-2), 4.19–3.99 (q, J=7.1 Hz, 2H, $CO_2CH_2CH_3$, two rotamers), 3.76–3.60 (m, 2 H, H-5), 2.62–2.38 (m, 1 H, H-3), 2.45+2.43 (s, 3 H, $PhCH_3$), 2.23–2.08 (m, 1 H, H-3), 1.25+1.08 (t, J=7.1 Hz, 3 H, $CO_2CH_2CH_3$); $^{13}C$ NMR (75.5 MHz, $CDCl_3$) δ 171.59, 171.39, 154.12, 153.64, 145.10, 135.96, 135.81, 133.14, 133.08, 129.88, 129.86, 128.25, 128.17, 127.85, 127.60, 127.48, 78.66, 78.00, 67.14, 67.11, 61.25, 61.17, 57.39, 57.07, 52.25, 51.87, 36.99, 35.86, 21.41, 13.84, 13.69; IR ($CHCl_3$) 1740, 1705, 1420, 1355, 1175 $cm^{-1}$; LRMS (EI, 70 eV) m/e 447 ($M^+$, 0.23), 374 (2), 202 (2), 158 (24), 91 (100); HRMS (EI, 40 eV) m/e 447.1337 (447.1351 calcd for $C_{22}H_{25}NO_7S$).

N-(Benzylozycarbonyl)-cis-4-cyano-L-proline ethyl ester. Finely powdered NaCN (0.85 g, 17 mmol) was added to a stirring mixture of the tosylate 2 (5.19 g, 11.6 mmol) in DMSO (15 mL). The reaction mixture was heated in an oil bath at 80° C. for 4h, then cooled to room temperature overnight. Brine (6 mL) and $H_2O$ (7 mL) were added to the orange-red reaction, and the resulting solution extracted with $Et_2O$ (5×15 mL). Drying of the combined organic extracts ($MgSO_4$) and removal of volatiles under vacuum gave a crude yellow syrup which was purified by flash chromatography (silica gel, using 4:3 ethyl ether-petroleum ether) yielding the desired cis nitrile ethyl ester (2.31 g, 66%) as a colorless viscous oil: TLC $R_f$ 0.15 (3:3:1 ethyl ether-petroleum ether-$CH_2Cl_2$); $[\alpha]^{25}_D-32°$ (c 1.11, $CHCl_3$; $^1H$ NMR (250 MHz, $CDCl_3$) δ 7.36–7.32 (m, 5 H), 5.21–5.04 (m, 2 H, $PhCH_2$), 4.48–4.37 (m, 1 H, H-2), 4.25 (q, J=7.1 Hz, 1 H, $CO_2CH_2CH_3$, one of two rotamers), 4.14–3.96 (m, 2 H, $CO_2CH_2CH_3$ and H-5), 3.80–3.70 (m, 1 H, H-5), 3.21–3.07 (m, 1 H, H-4), 2.78–2.64 (m, 1 H, H-3), 2.41–2.27 (m, 1 H, H-3), 1.29+1.16 (t, J=7.1 Hz, 3 H, $CO_2CH_2CH_3$); $^{13}C$ NMR (75.5 MHz, $CDCl_3$) δ 170.83, 170.60, 153.84, 153.48, 135.81, 135.73, 128.40, 128.32, 128.13, 128.08, 127.92, 127.82, 118.77, 118.66, 67.44, 67.38, 61.69, 58.22, 57.87, 49.44, 48.93, 34.20, 33.15, 27.02, 26.24, 13.89, 13.77; IR ($CHCl_3$) 2255, 1740, 1710, 1415, 1360, 1195, 1170, 1120 $cm^{-1}$; LRMS (CI, 70 eV, isobutane) m/e 303 ($MH^+$, 17), 259 (2), 169 (5), 91 (100); HRMS (EI, 40 eV) m/e 302.1247 (302.1266 calcd for $C_{16}H_{18}N_2O_4$).

N-(Benzyloxycarbonyl) -cis-4-carboxy-L-proline dimethyl ester (3). To a solution of the cis nitrile ester (1.91 g, 6.31 mmol) in methanol (15 mL) was added HCl (2.3 g, 63 mmol) in methanol (13 mL). After stirring at room temperature for 3.5 days, the reaction was quenched with $NaHCO_3$ (5.5 g, 65 mmol), then concentrated in vacuo. The residue was diluted with THF (30 mL) to extract the product off the sodium salts. Solids were removed by filtration, the filter cake washed with THF, and the combined filtrate and washings were concentrated. Purification of the resulting pale yellow residue by flash chromatography (silica gel, using 4:3 ethyl ether-petroleum ether) yielded 1.9 g (94%) of 3 as a colorless oil: TLC $R_f$ 0.17 (4:3 ethyl ether-petroleum ether); $[\alpha]^{24}_D-38°$ (c 1.09, $CHCl_3$); $^1H$ NMR (250 MH, $CDCl_3$) δ 7.37–7.27 (m, 5 H), 5.22–5.01 (m, 2 H, $PhCH_2$), 4.45–4.35 (m, 1 H, H-2), 3.98–3.67 (m, 2 H, H-5), 3.75+3.57

(s, 3 H, C-2 CO$_2$CH$_3$), 3.705+3.700 (s, 3 H, C-4 CO$_2$CH$_3$), 3.705+3.700 (s, 3 H, C-4 CO$_2$CH$_3$), 3.17–3.02 (m, 1 H, H-4), 2.59–2.31 (m, 2 H, H-3); $^{13}$C NMR (75.5 Mhz, CDCl$_3$) δ 172.23, 172.05, 171.98, 154.33, 153.80, 136.19, 136.15, 128.36, 128.30, 127.97, 127.92, 127.87, 127.74, 67.17, 67.06, 58.60, 58.29, 52.28, 52.20, 52.10, 48.83, 48.34, 42.21, 41.39, 32.92, 31.93; IR (CHCl$_3$) 2960, 1740, 1705, 1425, 1360, 1175, 1120 cm$^{-1}$; HRMS (EI, 24 eV) m/e 321.1225 (321.1212 calcd for C$_{16}$H$_{19}$NO$_6$).

N-(Benzyloxycarbonyl)-cis-4-carboxy-L-proline. The dimethyl ester 3 (0.761 g, 2.37 mmol) was suspended in 1:1 THF-H$_2$O (7 mL) and, with stirring, 4M NaOH (1.33 mL, 5.33 mmol) was added dropwise. During the addition, the reaction solution became homogeneous. Stirring was continued for 50 minutes, after which the reaction mixture was extracted twice with Et$_2$O (2×7 mL). Acidification of the aqueous layer with concentrated HCl caused precipitation of the oily product, which was extracted into ethyl acetate (3×8 mL). Before discarding, the ethyl ether layers from the previous extractions were washed with H$_2$O (2×4 mL) and the aqueous washings were added to the acidified aqueous layers. Now the total aqueous solution was extracted again with ethyl acetate (2×8 mL). The combined organic layers were dried (MgSO$_4$), filtered, and concentrated to afford 0.68 g (97%) of the dicarboxylate as a colorless solid which could be recrystallized from CH$_3$OH-Et$_2$O, but was sufficiently pure to be used directly in the step: mp 175°–176° C.; [α]$^{25}_D$ –27° (c 1.05, CH$_3$OH); $^1$H NMR (250 MHz, CD$_3$OD) δ 7.40–7.26 (m, 5 H), 5.18–5.03 (m, 2 H, PhCH$_2$), 4.40–4.31 (m, 1 H, H-2), 3.85 (app dd, J=10.7, 8.2 Hz, 1 H, H-5), 3.75–3.67 (m 1 H, H-5), 3.23–3.19 (m, 1 H, H-4), 2.66–2.51 (m, 1 H, H-3), 2.38–2.24 (m, 1 H, H-3); $^{-13}$C NMR (75.5 MHz, CD$_3$OD) δ 175.65, 175.35, 175.22, 156.35, 156.05, 137.86, 137.73, 129.55, 129.46, 129.13, 129.00, 128.88, 128.64, 68.34, 60.18, 59.85, 50.19, 49.74, 43.42, 42.67, 34.20, 33.27; IR (KBr) 3600–2300 (broad), 1740, 1685, 1635, 1450, 1415, 1360, 1240, 1140. Anal. Calcd for C$_{14}$H$_{15}$NO$_6$: C, 57.34; H, 5.16; N, 4.78. Found: C, 57.25; H, 5.25; N, 4.68.

cis-4-Carboxy-L-proline (4). N-CBZ-cis-4-carboxy-L-proline (0.455 g, 1.55 mmol) was dissolved in methanol (37 mL) and transferred into a Parr shaker bottle. After adding 10% Pd-C (0.080 g), the mixture was shaken under an atmosphere of hydrogen at 48–50 psi for 0.5 h on the Parr apparatus. The catalyst was removed by filtration through Celite. The filter-cake was washed with water and the combined filtrate and washings were concentrated in vacuo to yield a white solid, which was recrystallized from H$_2$O-ethanol-acetone to yield 0.206 g (84%) of 4 as colorless prisms: mp 225°–226° C.; [α]$^{25}_D$ –40° (c 1.02, H$_2$O); $^1$H NMR (250 MHz, D$_2$O) δ 4.25 (dd, J=8.6, 7.4 Hz, 1 H, H-2), 3.72 (dd, J=12.0, 6.7 Hz, 1 H, H-5), 3.57 (dd, J=12.0, 8.0 Hz, 1 H, H-5), 3.38 (m, 1H, H-4), 2.71 (app dt, J=13.7, 8.6 Hz, 1 H, H-3), 2.35 (app overlapping dt, J=13.7, 7.4 Hz, 1 H,H-3); $^{13}$C NMR (75.5 MHz, D$_2$O) δ 178.75, 176.25, 63.87, 50.16, 45.43, 34.78; IR (KBr) 3600–2200 (broad), 3080, 1690, 1560, 1340, 1230 cm$^{-1}$; MS (CI, 70 eV, methane) m/e 160 (MH$^+$, 14), 114 (100). Anal. Calcd for C$_6$H$_9$NO$_4$: C, 45.28; H, 5.70; N, 8.80. Found: C, 45.31; H, 5.51; N, 8.75.

N-(Benzyloxycarbonyl)-cis-4-hydroxy-L-proline ethyl ester. N-CBZ-trans-4-hydroxy-L-proline (2.65 g, 10.0 mmol) was dissolved in acetone (20 mL) and cooled to −5° C. in an ice-salt water bath. Jones reagent (7.5 mL, 20.0 mmol) was added, the ice bath was removed, and the reaction was stirred at room temperature for 2.25 h before quenching the excess Jones reagent with isopropanol (1 mL). After stirring for 2 h, the green solution was decanted from the dark green precipitate and concentrated in vacuo. The residue was partitioned between ethyl acetate (20 mL) and brine (10 mL). After separating the layers, the organic layer was washed once more with brine (10 mL) and the aqueous layer from this extraction was combined with that from the previous extraction. The total aqueous solution was washed with ethyl acetate (15 mL) and this organic layer combined with the previous one. Now the aforementioned dark green precipitate was dissolved in water (50 mL), saturated with NaCl, and extracted with ethyl acetate (5×10 mL). All organic layers were combined, dried (MgSO$_4$), and concentrated in vacuo to yield the crude N-CBZ-4-keto-L-proline as a yellow oil, which was used without further purification. The ketone was dissolved in methanol (50 mL) and the reaction flask was cooled to 0° C. in an ice bath. A solution of NaBH$_4$ (1.44 g, 38.0 mmol) in water (5 mL) was added dropwise. The reaction was allowed to sit in the refrigerator (−5° C.) for 20 h. Volatiles were removed in vacuo. The residue was diluted with H$_2$O (10 mL) and acidified to pH 2–3 with concentrated HCl, then extracted with ethyl acetate (2×10 mL). The aqueous layer was saturated with NaCl and again extracted with ethyl acetate (2×10 mL). Now the aqueous layer was concentrated to a white solid, which was diluted with 2:1 ethyl acetate-THF (30 mL) and heated at mild reflux for 0.5 h. Salts were removed by filtration through celite. This filtrate and the organic layers from the previous extractions were combined, dried (MgSO$_4$) and concentrated to yield the crude N-CBZ-cis-4-hydroxy-L-proline as a yellow oil. This residue was dissolved in ethanol (150 mL) containing a catalytic amount of p-toluenesulfonic acid monohydrate (0.25 g, 1.31 mmol). The reaction mixture was heated at reflux with the collection of wet ethanol in a Dean-Stark trap. After 36 h, the trap was emptied whenever full until the total reaction volume was about 50 mL. After neutralizing the tosic acid with NaHCO$_3$ (0.5 g, 6.0 mmol), the solvent was removed in vacuo, the residue was diluted with ethyl acetate (75 mL) and the mixture stirred vigorously for 0.5 h to extract the product from the sodium salts. Solids were removed by filtration through Celite-K$_2$CO$_3$ and the filter cake was washed with ethyl acetate (15 mL). The combined filtrate and washings were concentrated. Purification of the resulting residue by flash chromatography (silica gel, using ethyl ether) provided the cis hydroxy ethyl ester (2.1 g, 83%) as a yellow oil: TLC R$_f$ 0.18 (ethyl ether); $^1$H NMR (250 MHz, CDCl$_3$) δ 7.37–7.27 (m, 5 H), 5.22–5.04 (m, 2 H, PhCH$_2$), 4.50–4.35 (m, 2 H, H-2 and H-4), 4.25 (q, J=7.1 Hz, 1 H, CO$_2$CH$_2$CH$_3$, one of two rotamers), 4.08 (app qd, J=7.1, 1.7 Hz, 1 H, CO$_2$CH$_2$CH$_3$), 3.76–3.45 (m, 3 H, H-5 and OH), 2.41–2.26 (m, 1 H, H-3), 2.16–2.08 (m, 1 H, H-3), 1.30+1.14 (t, J=7.1 Hz, 3 H, CO$_2$CH$_2$CH$_3$); IR (CHCl$_3$) 3650–3250 (broad), 2990, 1735, 1705, 1420, 1355, 1200, 1125, 1080 cm$^1$; LRMS (CI, 70 eV, isobutane) m/e 294 (M$^+$, 100), 250 (34), 220 (9), 91 (29); HRMS (EI, 22 eV) m/e 293.1272 (293.1263 calcd for C$_{15}$H$_{19}$NO$_5$).

N-(Benzyloxycarbonyl)-cis-4-tosyloxy-L-proline ethyl ester (5). To a solution of N-CBZ-cis-4-hydroxy-L-proline ethyl ester (6.4 g, 22 mmol) and anhydrous pyridine (5.3 mL, 5.2 g, 65 mmol) in CHCl$_3$ (35 mL) was added p-toluenesulfonyl chloride (8.3 g, 44 mmol) in one portion. After stirring at room temperature for 7 days, the reaction was diluted with CH$_2$Cl$_2$ (100 mL) and pyridine removed by extraction with 10% HCl (4×13 mL). The organic layer was dried (MgSO$_4$) and concentrated to a yellow oil which was purified by flash chromatography (silica gel, using 5:4 petroleum ether-ether) affording 7.8 g (80%) of 5 as colorless needles: mp 91°–92° C.; TLC $R_f$ 0.15 (4:2 ethyl ether-petroleum ether); $[\alpha]^{25}_D$ –26° (c 1.1, $CHCl_3$); $^1H$ NMR (250 MHz, $CDCl_3$) δ 7.75 (app d, J=8.4 Hz, 2 H), 7.34–7.28 (m, 7 H), 5.18–5.04 (m, 3 H, $PhCH_2$ and H-4), 4.52–4.41 (m, 1 H, H-2), 4.20–4.02 (m, 2 H, $CO_2CH_2CH_3$), 3.78–3.62 (m, 1 H, H-5), 2.48–2.37 (m, 2 H, H-3), 2.45+2.44 (s, 3 H, $PhCH_3$, two rotamers), 1.22+1.14 (t, J=7.1 Hz, 3 H, $CO_2CH_2CH_3$); $^{13}C$ NMR (75.5 MHz, $CDCl_3$) δ 170.89, 170.57, 154.20, 153.89, 145.12, 145.09, 136.11, 133.88, 129.91, 129.85, 128.38, 128.32, 128.03, 127.98, 127.86, 127.77, 127.58, 78.62, 77.74, 67.21, 67.15, 61.47, 57.53, 57.30, 52.25, 51.99, 37.07, 35.98, 21.59, 13.92, 13.85; IR ($CHCl_3$) 2995, 1745, 1700, 1415, 1360, 1175, 1120, 1050, 1020 $cm^1$. Anal. Calcd for $C_{22}H_{25}NO_7S$: C, 59.05; H, 5.63; N, 3.13. Found: C, 59.08; H, 5.54; N, 3.11.

N-(Benzyloxycarbonyl)-trans-4-cyano-L-proline ethyl ester. Finely powdered NaCN (0.49 g, 10 mmol) was suspended in a stirring mixture of 5 (3.0 g, 6.7 mmol) in DMSO (7 mL). The reaction flask was heated in an oil bath at 80° C. for 3 h, during which time the NaCN had completely dissolved and the reaction mixture had turned a deep orange color. After cooling to room temperature, the reaction was diluted with brine (3 mL) and $H_2O$ (4 mL), then extracted with $Et_2O$ (5×11 mL). The combined organic layers were dried ($MgSO_4$) and concentrated to a yellow syrup which was purified by flash chromatography (silica gel, using 1:1 ethyl ether-petroleum ether) yielding 1.42 g (70%) of the N-CBZ-trans-4-cyano-L-proline ethyl ester as a colorless viscous oil: TLC $R_f$ 0.22 (4:2 ethyl ether-petroleum ether); $[\alpha]^{24}_D$ –39° (c 1.05, $CHCl_3$); $^1H$ NMR (250 MHz, $CDCl_3$) δ 7.38–7.27 (m, 5 H), 5.21–5.03 (m 2 H, $PhCH_2$), 4.55–4.45 (m, 1 H, H-2), 4.21 (q, J=7.1 Hz, 1 H, $CO_2CH_2CH_3$, one of two rotamers), 4.09–3.94 (m, 2 H, $CO_2CH_2CH_3$ and H-5), 3.80–3.67 (m, 1 H, H-5), 3.35–3.21 (m, 1 H, H-4), 2.62–2.34 (m, 2 H, H-3), 1.28+1.13 (t, J=7.1 Hz, $CO_2CH_2CH_3$, two rotamers); IR ($CHCl_3$) 2995, 2900, 2250, 1740, 1705, 1420, 1355, 1195, 1125, 1020 $cm^{-1}$; LRMS (CI, 70 eV, isobutane) m/e 303 ($MH^+$, 66), 259 (44), 91 (100); HRMS (EI, 21 eV) m/e 302.1264 (302.1266 calcd for $C_{16}H_{18}N_2O_4$).

N-(Bensyloxycarbonyl)-trans-4-carboxy-L-proline dimethyl ester (6). To a solution of N-CBZ-trans-4-cyano-L-proline ethyl ester (1.19 g, 3.95 mmol) in methanol (8 mL) was added HCl (1.44 g, 39.5 mmol) in methanol (10 mL). After 4 days, the reaction was quenched with $NaHCO_3$ (3.7 g, 44 mmol), then concentrated in vacuo. The residue was diluted with THF (25 mL) to extract the product off the sodium salts. Solids were removed by filtration, the filter cake was washed with THF, and the combined filtrate and washings were concentrated. Purification of the residue by flash chromatography (silica gel, using 1:1 ethyl ether-petroleum ether) afforded 1.2 g (94%) of 6 as a colorless oil: TLC $R_f$ 0.23 (4:3 ethyl ether-petroleum ether); $[\alpha]^{27}_D$ –43° (c 1.06, $CHCl_3$); $^1H$ NMR (250 MHz, $CDCl_3$) δ 7.35–7.28 (m, 5 H), 5.22–5.01 (m, 2 H, $PhCH_2$), 4.55–4.44 (m, 1 H, H-2), 3.92–3.84 (m, 1 H, H-5), 3.77–3.64 (m 1 H, H-5), 3.75+3.58 (s, 3 H, C-2 $CO_2CH_3$, two rotamers), 3.70+3.69 (s, 3 H, C-4 $CO_2CH_3$), 3.32–3.15 (m, 1 H, H-4), 2.59–2.40 (m, 1 H, H-3), 2.31–2.19 (m, 1 H, H-3); $^{13}C$ NMR (75.5 MHz, $CDCl_3$) δ 172.51, 172.48, 172.37, 172.32, 154.39, 153.79, 136.19, 128.35, 128.28, 127.94, 127.89, 127.78, 127.66, 67.15, 67.03, 58.70, 58.36, 52.34, 52.17, 48.94, 48.29, 41.68, 40.86, 33.29, 32.40; IR ($CHCl_3$) 2960, 1740, 1705, 1420, 1355, 1195, 1180, 1125 $cm^{-1}$; LRMS (CI, 70 eV, isobutane) m/e 322 ($MH^+$, 100), 278 (42), 262 (4), 186 (17), 91 (65); HRMS (EI, 21 eV) m/e 321.1206 (321.1212 calcd for $C_{16}H_{19}NO_6$).

N-(Benzyloxycarbonyl)-trans-4-carboxy-L-proline. The dimethyl ester 6 (0.502 g. 1.56 mmol) was suspended in 3.2 THF-$H_2O$ (5 mL) and, with stirring, 4M NaOH (0.90 mL, 3.6 mmol) was added dropwise. After stirring for 55 minutes, the reaction mixture was extracted with $Et_2O$ (2×5 mL). Acidification of the aqueous layer with concentrated HCl caused precipitation of the oily product, which was removed from the aqueous solution by extraction with ethyl acetate (3×6 mL). Before discarding, the $Et_2O$ layers from the previous extraction were washed with $H_2O$ (2×4 mL) and these aqueous washings were added to the acidic aqueous layers. Now the total aqueous solution was extracted with ethyl acetate (2×6 mL), and all of the ethyl acetate layers were combined, dried ($MgSO_4$), filtered, and concentrated to afford a thick, sticky, colorless oil which eventually crystallized upon standing at room temperature to yield 0.480 g (100%) of N-(Benzyloxycarbonyl)-trans-4-carboxy-L-proline: mp 98°–100° C.; $[\alpha]^{25}_D$ –37° (c 0.84, $CH_3OH$); $^1H$ NMR (300 MH, $CD_3OD$) δ 7.36–7.28 (m, 5 H), 5.15–5.01 (m, 2 H, $PhCH_2$), 4.45–4.39 (m, 1 H, H-2), 3.81–3.67 (m, 2 H, H-5), 3.27–3.14 (m, 1 H, H-4), 2.59–2.44 (m, 1 H, H-3), 2.30–2.21 (m, 1 H, H-3); $^{13}C$ NMR (75.5 MHz $CD_3COCD_3$) δ 173.73, 173.62, 17338, 155.06, 154.56, 137.89, 137.85, 129.15, 129.04, 128.58, 128.39, 128.07, 67.24, 67.16, 59.61, 59.14, 49.78, 49.17, 42.42, 41.50, 34.15, 33.11; IR ($CHCl_3$) 3600–2300 (broad), 1720, 1705, 1420, 1360, 1235, 1135 $cm^1$; HRMS (EI, 21 eV) m/e 293.0901 (293.0899 calcd for $C_{14}H_{15}NO_6$).

trans-4-Carboxy-L-proline (7). N-CBZ-trans-4-carboxy-L-proline (0.458 g, 1.56 mmol) was dissolved in methanol (50 mL) and transferred into a Parr shaker bottle. After adding 10% Pd-C (0.080 g), the mixture was shaken under an atmosphere of hydrogen at 48–50 psi for 0.5 h on the Parr apparatus. The catalyst was removed by filtration through Celite and the filter cake was washed with water. The combined filtrate and washings were concentrated in vacuo to yield a white solid, which was recrystallized from $H_2O$-EtOH-acetone to yield 0.187 g (75%) of 7 as colorless prisms: mp 219°–220° C. (lit. $^{18}$ mp 223°–225° C.); $[\alpha]^{25}_D$ –54° (c 1.04, $H_2O$) [lit. $^{18}$ $[\alpha]^{20}_D$ –46.0° (c 1.0, $H_2O$)]; $^1H$ NMR (300 MHz, $D_2O$) δ 4.28 (dd, J=8.6, 7.3 Hz, 1 H, H-2), 3.68–3.57 (m, 2 H, H-5), 3.38–3.29 (m, 1 H, H-4), 2.59 (ddd, J=13.7, 8.6, 6.0 Hz, 1 H, H-3), 2.42 (ddd, J=13.7, 8.1, 7.3 Hz, 1 H, H-3); $^{13}C$ NMR (75.5 MHz, $D_2O$) δ 178.99, 176.30, 63.67, 50.32, 45.24, 35.18; IR (KBr) 3600–2200 (broad), 1720, 1610, 1515, 1360, 1335, 1285, 1220, 1185 $cm^{-1}$; LRMS (EI, 70 eV) m/e 159 ($M^+$, 19), 114 (100), 87 (53), 68 (92). Anal. Calcd for $C_6H_9NO_4$: C, 45.28; H, 5.70; N, 8.80. Found: C, 45.21; H, 5.64; N, 8.68.

N-(Benzyloxycarbonyl)-cis-4-hydroxy-D-proline. Cis-4-hydroxy-D-proline 8 (10.0 g, 76.3 mmol) was dissolved in $H_2O$ (165 mL) containing $NaHCO_3$ (16.0 g, 190 mmol). Benzyl chloroformate (12.5 mL, 15.0 g, 87.7 mmol) in toluene (40 mL) was added to this stirring solution at room temperature over 30 minutes using a dropping funnel. The reaction was stirred for 16 h. By this time, $CO_2$ evolution had ceased, and the two phases were separated. Excess benzyl chloroformate was removed from the aqueous layer by washing with ether (3×50 mL). The aqueous phase was cooled in an ice bath and acidified to pH2 with concentrated HCl, causing precipitation of the oily product. This oil was extracted from the aqueous layer by repeated washings with ethyl acetate (5×50 mL). Further acidification of the aqueous layer produced no more precipitate, indicating the extraction was complete. The combined organic layers were washed with brine, dried ($MgSO_4$), and concentrated to a colorless viscous oil, which crystallized upon standing at room temperature to provide 19.42 g (96%) of N-CBZ-cis-4-hydroxy-D-proline: mp 110°–111° C. (lit. $^{19}$ mp 110.5°–111.5° C.); $[\alpha]^{25}_d$+24.4° (c 1.0, $CHCl_3$) ]lit. $^{19}$ $[\alpha]^{25}_D$+26.3° (c 1.0, $CHCl_3$)].

N-(Benzyloxycarbonyl)-cis-4-hydroxy-D-proline ethyl ester. N-CBZ-cis-4-hydroxy-D-proline (5.00 g, 18.8 mmol) was esterified by refluxing in ethanol (300 mL) containing a catalytic amount of p-toluenesulfonic acid monohydrate (0.3 g, 1.6 mmol). Wet ethanol was collected in a Dean-Stark trap. After 16 h, the trap was emptied whenever full until the reaction volume had decreased to about 50 mL. The tosic acid was neutralized with an excess of $NaHCO_3$ (0.5 g, 6 mmol). After removal of volatiles in vacuo, the residue was diluted with ethyl acetate (100 mL) and the mixture stirred for 0.5 h to remove the oily product from the sodium salts. Solids were removed by filtration through Celite and the filter cake was washed with ethyl acetate (50 mL). Concentration of the combined filtrate and washings in vacuo provided 5.6 g (100%) of the crude cis hydroxy ester as a colorless oil: $^1H$ NMR and IR spectra were identical in all respects to those of the enantiomer N-(benzyloxycarbonyl)-cis-4-hydroxy-L-proline ethyl ester; $^{13}C$ NMR (75.5 MHz, $CDCl_3$) δ 174.54, 174.35, 154.87, 154.21, 136.24, 136.11, 128.39, 128.31, 127.99, 127.96, 127.83, 127.74, 70.99, 70.01, 67.18, 61.88, 61.72, 58.17, 57.77, 55.90, 55.60, 38.54, 37.64, 13.93, 13.80; LRMS (CI, 70 eV, isobutane) m/e 294 ($MH^+$, 81), 250 (100), 220 (23), 91 (66); HRMS (EI, 50 eV) m/e 293.1267 (293.1263 calcd for $C_{15}H_{19}NO_5$).

N-(Benzyloxycarbonyl)-cis-4-tosyloxy-D-proline ethyl ester (9). Using previously described procedures, N-CBZ-cis-4-hydroxy-D-proline (4.7 g, 16 mmol) was converted to 6.6 g (92%) of 9 as colorless needles: mp 91°–92° C. $[\alpha]^{26}_D +27°$ (c 1.1, $CHCl_3$); Spectra were identical in all respects to those of the enantiomer 5. Anal. Calcd for $C_{22}H_{25}NO_7S$: C, 59.05; H, 5.63; N, 3.13 Found: C, 58.87; H, 5.68; N, 3.07.

N-(Benzyloxycarbonyl)-trans-4-cyano-D-proline ethyl ester. Treatment of 9 (1.0 g. 2.23 mmol) with NaCN in DMSO provided N-CBZ-trans-4-cyano-D-proline ethyl ester (0.48 g. 1.6 mmol, 72%) as a colorless oil: $[\alpha]^{25}_D +40°$ (c 1.0, $CHCl_3$); $^1H$ NMR and IR spectra were identical in all respects to those of the enantiomer N-(benzyloxycarbonyl)-trans-4-cyano-L-proline ethyl ester; $^{13}C$ NMR (75.5 MHz, $CDCl_3$) δ 171.21, 171.13, 153.86, 153.42, 135.77, 135.70, 128.38, 128.29, 128.10, 128.03, 127.86, 127.74, 118.73, 118.61, 67.45, 67.38, 61.65, 61.56, 58.02, 57.61, 49.33, 48.80, 34.39, 33.38, 26.82, 26.15, 13.92, 13.81; LRMS (CI, 70 eV, isobutane) m/e 303 ($MH^+$, 100), 259 (84), 91 (85); HRMS (EI, 70 eV) m/e 302.1253 (302.1266 calcd for $C_{16}H_{18}N_2O_4$).

N-(Benzyloxycarbonyl)-trans-4-carboxy-D-proline dimethyl ester (10). Using the procedure described earlier for preparation of the L enantiomer 6, N-CBZ-trans-4-cyano-D-proline ethyl ester (0.47 g, 1.6 mmol) was converted to 0.47 g (94%) of 10 as a colorless oil: $[\alpha a]^{28}_D +41°$ (c 1.13, $CHCl_3$). Spectra were identical in all respects to those of the enantiomer 6: LRMS (CI, 70 eV, isobutane) m/e 322 ($MH^+$, 100), 278 (48), 262 (4), 186 (16), 91 (28); HRMS (EI, 70 eV) m/e 321.1231 (321.1212 calcd for $C_{16}H_{19}NO_6$).

N-(Benzyloxycarbonyl)-trans-4-carboxy-D-proline. The dimethyl ester 10 (0.336 g, 1.05 mmol) was saponified as described above to yield 0.294 g (96%) of N-CBZ-trans-4-carboxy-D-proline as a colorless, extremely viscous oil: $[\alpha]^{24}_D +39°$ (c 0.51, $CH_3OH$); Spectra were identical in all respects to those of the enantiomer N-(benzyloxycarbonyl)-trans-4-carboxy-L-proline.

trans-4-Carboxy-D-proline (11). Hydrogenation of the crude N-CBZ-trans-4-carboxy-D-proline (0.294 g, 1.00 mmol) gave 0.138 g (87%) of 11 as colorless prisms: mp 219°–220° C.; $[\alpha]^{25}_D +51°$ (c. 1.04, $H_2O$). Spectra were identical in all respects to those of the enantiomer 7; HRMS (EI, 22 eV) m/e 160.0613 (160.0610 calcd for $C_6H_9NO_4 + H^+$), 159.0530 (159.0532 calcd for $C_6H_9NO_4$). Anal. Calcd for $C_6H_9NO_4$: C, 45.28; H, 5.70; N, 8.80. Found C, 44.82; H, 5.68; N, 8.71.

N-(Bensyloxycarbonyl)-trans-4-acetoxy-D-proline ethyl ester. To a solution of the tosylate 9 (4.00 g, 8.94 mmol) in acetone (25 mL) was added $n-Bu_4NOAc$ (4.04 g, 13.4 mmol) and the resulting mixture was stirred at room temperature for 20 h. After concentrating the reaction mixture, the resulting yellow oil was diluted with $H_2O$ (5 mL) and extracted with ethyl ether (5×11 mL). The combined organic layers were dried ($MgSo_4$) and concentrated. Purification of the crude product by flash chromatography (silica gel using 4:3 petroleum ether-ether) provided 2.49 g (83%) of the pure acetate as a colorless oil: TLC $R_f$ 0.30 (4:2 ethyl ether-petroleum ether); $[\alpha]^{26}_D +48°$ (c 1.15, $CHCl_3$); $^1H$ NMR (250 MH, $CDCl_3$) δ 7.37–7.33 (m, 5 H), 5.32–5.27 (m, 1 H, H-4), 5.21–5.04 (m, 2 H, $PhCH_2$), 4.47+4.43 (app t, J=8.0 Hz, 1 H, H-2, two rotamers), 4.22+4.02 (q, J=7.1 Hz, 2 H, $CO_2CH_2CH_3$), 3.83–3.63 (m, 2 H, H-5), 2.48–2.36 (m, 1 H, H-3), 2.28–2.15 (m, 1 H, H-3), 2.054+2.045 (s, 3 H, $CH_3CO_2$), 1.28+1.11 (t, J=7.1 Hz, 3 H, $CO_2CH_2CH_3$); $^{13}C$ NMR (75.5 MHz, $CDCl_3$) δ 172.08, 171.86, 170.28, 170.23, 154.61, 154.07, 136.17, 136.02, 128.36, 128.29, 127.95, 127.78, 72.48, 71.73, 67.20, 67.16, 61.33, 61.22, 57.86, 57.60, 52.47, 52.02, 36.49, 35.46, 20.93, 13.99, 13.85; IR ($CHCl_3$) 1740, 1705, 1420, 1355, 1245, 1200, 1170, 1130, 1070, 1028 $cm^{-1}$; LRMS (CI, 70 eV, isobutane) m/e 336 ($MH^+$, 100), 292 (36), 91 (33); HRMS (EI, 70 eV) m/e 335.1349 (335.1369 calcd for $C_{17}H_{21}NO_6$).

N-(Benzyloxycarbonyl)-trans-4-hydroxy-D-proline ethyl ester. To a stirring solution of N-CBZ-trans-4-acetoxy-D-proline (2.45 g, 7.31 mmol) in ethanol (50 mL) was added freshly prepared NaOEt/EtOH (0.017 g, 0.7 mmol of Na dissolved in 1 mL of EtOH). After stirring at room temperature for 20 minutes, the reaction was quenched with $NH_4Cl$ (0.1 g), and concentrated in vacuo to an oily solid. The desired alcohol was isolated (2.01 g, 94%) as a colorless oil by diluting the residue with ethyl ether (50 mL), filtering the solution through Celite, washing the filter cake with ethyl ether, and concentrating the combined filtrate and washings in vacuo. The alcohol was sufficiently pure to use directly in the next step: $[\alpha]^{25}_D +59°$ (c, 1.04 $CHCl_3$); Spectra were identical in all respects to those of the enantiomer N-(benzyloxycarbonyl)-trans-4-hydroxy-L-proline ethyl ester; LRMS (CI, 70 eV, isobutane) m/e 294 ($MH^+$, 100), 250 (98), 220 (24), 158 (25), 91 (89); HRMS (EI, 50 eV) m/e 293.1272 (293.1263 calcd for $C_{15}H_{19}NO_5$).

N-(Benyloxycarbonyl)-trans-4-tosyloxy-D-proline ethyl ester (12). The tosylate 12 (2.24 g, 97%) was prepared as a colorless oil from N-CBZ-trans-4-hydroxy-D-proline ethyl ester (1.51 g, 5.16 mmol) by the procedure described previously for making the L enantiomer: $[\alpha]^{24}_D +29°$ (c 1.01, $CHCl_3$). Spectra were identical in all respects to those of the enantiomer 2; HRMS (EI, 26 eV) m/e 447.1331 (447.1351 calcd for $C_{22}H_{25}NO_7S$).

N-(Benzyloxycarbonyl)-cis-4-cyano-D-proline ethyl ester. The tosylate 12 (2.02 g, 4.53 mmol) was treated with NaCN in DMSO at 80° C. to provide, after workup, the cis nitrile ester (0.88 g, 64%) as a colorless oil: $[\alpha]^{25}_D +32°$ (c 1.04, $CHCl_3$); Spectra were identical in all respects to those of the enantiomer N-(benzyloxycarbonyl)-cis-4-cyano-L-proline ethyl ester; HRMS (EI, 22 eV) m/e 302.1255 (302.1266 calcd for $C_{16}H_{18}NO_4$).

N-(Benzylozycarbonyl)-cis-4-carboxy-D-proline dimethyl ester (13). The N-CBZ-cis-4-cyano-D-proline ethyl ester (0.755 g, 2.50 mmol) was treated with wet methanolic HCl and worked up as described above to provide the dimethyl ester 13 (0.746 g, 2.32 mmol, 93%) as a colorless oil: $[\alpha]^{26}{}_D$+40° (c 1.15, CHCl$_3$); Spectra were identical in all respects to those of the enantiomer 3; HRMS (EI, 22 eV) m/e 321.1226 (321.1212 calcd for C$_{16}$H$_{19}$NO$_6$.

N-(Benzyloxycarbonyl)-cis-4-carboxy-D-proline. Saponification of the cis dimethyl ester 13 (0.502 g, 1.56 mmol) gave 0.44 g (96%) of the desired cis dicarboxylate as colorless prisms: mp 175°–176° C; $[\alpha]^{26}{}_D$+30° (c 1.10, CH$_3$OH); Spectra were identical in all respects to those of the enantiomer N-(benzyloxycarbonyl)-cis-4-carboxy-L-proline. Anal. Calcd for C$_{14}$H$_{15}$NO$_6$: C, 57.34; H, 5.16; N, 4.78. Found: C, 57.43; H, 5.18; C, 4.68.

cis-4-Carboxy-D-proline (14). Hydrogenation of the crude N-CBZ-cis-4-carboxy-D-proline (0.398 g, 1.36 mmol) gave 0.167 g (77%) of 14 as colorless prisms: mp 224°–225° C.; $[\alpha]^{24}{}_D$+37° (c 1.01, H$_2$O); Spectra were identical in all respects to those of the enantiomer 4. Anal. Calcd for C$_6$H$_9$NO$_4$: C, 45.28; H, 5.70; N, 8.80. Found: C, 45.16; H, 5.54; N, 8.58.

EXAMPLE VI
General procedure for preparation of the Mosher amides

In a typical preparation, a solution of the N-CBZ-4-carboxyproline dimethyl ester (0.059 g, 0.18 mmol) in ethanol (12 mL) was hydrogenated on a Parr apparatus at 50 psi over 10% Pd-C (0.011 g) for 0.5 h. The catalyst was removed by filtration through Celite, and the filter cake was washed with ethanol. The combined filtrate and washings were concentrated in vacuo. The residue was diluted with THF and again concentrated in vacuo. After dissolving the colorless residue in pyridine (1 mL), the crude 4-carboxyproline dimethyl ester was treated with (S)-(–)-α-methoxy-α-(trifluoromethyl)phenylacetyl chloride (0.07 g, 0.28 mmol) and the resulting mixture stirred at room temperature for 16 h. The brown colored reaction was quenched with H$_2$O (1.5 mL) and stirred for 0.5 h. After dilution with Et$_2$O (10 mL) and separation of the layers, the organic layer was washed successively with 10% HCl (2×5 mL), saturated NaHCO$_3$ (2×5 mL) and H$_2$O (5 mL). The organic layer was dried (MgSO$_4$) and concentrated to an orange oil.

The diasteromeric purity of the crude Mosher amide derivatives of the cis-4-carboxyproline dimethyl esters was determined by analysis with 300-MHz $^1$H NMR. For each derivative, the signals corresponding to the H-4 and one H-5 proton were chosen for analysis.

Mosher amide of cis-4-carboxy-L-proline dimethyl ester: d 3.18 (dd, J=11.4, 7.5 Hz, 1 H, H-5), 2.73–2.63 (m, 1 H, H-4); de >95%.

Mosher amide of cis-4-carboxy-D-proline dimethyl ester: d 3.01–2.86 (m, 2H, H-4 and H-5); de >95%.

The diasteromeric purity of the crude Mosher amide derivatives of the trans-4-carboxyproline dimethyl esters was determined by analysis with 250-MHz $^1$H NMR. For each derivative, the signal corresponding to H-2 was chosen for analysis.

Mosher amide of trans-4-carboxy-L-proline dimethyl ester: d 4.73 (dd, J=8.5, 6.9 Hz, 1 H, H-2); de >95%.

Mosher amide of trans-4-carboxy-D-proline dimethyl ester: d 4.66 (dd, J=8.7, 4.7 Hz, 1 H, H-2); de >95%.

We claim:

1. A method of inhibiting the transport of a neurotransmitter away from a synapse comprising contacting said synapse with a compound selected from the group consisting of compounds having the structure:

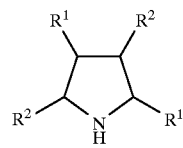

wherein $R^1$=CO$_2$R$^3$; P(OR$^3$)$_2$; P(OH)(OR$^3$); SO$_3$R$^3$; or CONHR$^3$ in any combination;

$R^2$=OR$^3$, NR$^3{}_2$, alkyl, or H; and.

$R^3$=alkyl, substituted alkyl, or H, wherein the compounds are capable in inhibiting the uptake of L-alutamate into synaptosomes, and wherein said neurotransmitter is capable of binding a transporter which binds L-glutamate.

2. The method of claim 1, wherein the neurotransmitter is L-glutamate.

3. The method of claim 1, wherein the neurotransmitter is L-aspartate.

4. The method of claim 1, wherein the compound is L-trans pyrrolidine-2,4-dicarboxylate.

5. The method of claim 1, wherein the compound is the L-trans isomer of Pyrrolidine-2,4-Dicarboxylate Diastereomer.

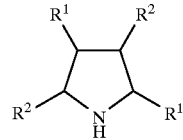

wherein $R^1$=CO$_2$R$^3$; P(OR$^3$); —P(OH)(OR$^3$); or CONHR$^3$ in any combination;

$R^2$=OR$^3$, NR$^3{}_2$, alkyl, or H; and $R^3$=alkyl, substituted alkyl or H.

6. The method of claim 1, wherein said neurotransmitter is an excitatory amino acid or an excitatory amino acid analogue.

7. The method of claim 2, wherein the compound is L-trans pyrrolidine-2,4-dicarboxylate.

* * * * *

UNITED STATES PATENT AND TRADEMARK OFFICE
CERTIFICATE OF CORRECTION

PATENT NO. : 5,942,537
DATED : August 24, 1999
INVENTOR(S) : Chamberlin et al.

It is certified that error appears in the above-identified patent and that said Letters Patent is hereby corrected as shown below:

Column 9,
Line 61, delete "$C_{15}H_1NO_5$)." and replace therefor with -- $C_{15}H_{19}NO_5$). --.

Column 10,
Line 48, please delete "$cm^{1-}$;" and replace therefor with -- $cm^{-1}$; --.

Column 14,
Lines 66-67, please delete "| $\alpha|^{25}_d$+24.4° (c 1.0. CHCl$_3$) | lit. $^{19}$ | $\alpha^{25}{}_D$+26.3 (c 1.0.CHCl$_3$ | ." and replace therefor with -- [$\alpha$]$^{25}_d$+24.4° (c 1.0, CHCl$_3$) [lit. $^{19}$ [$\alpha^{25}{}_D$+26.3° (c 1.0, CHCl$_3$)]. --

Column 18,
Line 26, please delete "L-alutamate" and replace with -- L-glutamate --.

Signed and Sealed this

First Day of June, 2004

JON W. DUDAS
*Acting Director of the United States Patent and Trademark Office*